United States Patent
Burns

(10) Patent No.: US 9,402,884 B2
(45) Date of Patent: Aug. 2, 2016

(54) METHODS OF TREATING PULMONARY SARCOIDOSIS

(71) Applicant: Barry Burns, Brooklyn, NY (US)

(72) Inventor: Barry Burns, Brooklyn, NY (US)

(*) Notice: Subject to any disclaimer, the term of this patent is extended or adjusted under 35 U.S.C. 154(b) by 0 days.

(21) Appl. No.: 14/846,266

(22) Filed: Sep. 4, 2015

(65) Prior Publication Data
US 2016/0067317 A1    Mar. 10, 2016

Related U.S. Application Data

(60) Provisional application No. 62/047,361, filed on Sep. 8, 2014.

(51) Int. Cl.
| | |
|---|---|
| *A61K 38/46* | (2006.01) |
| *A61K 31/10* | (2006.01) |
| *A61K 9/00* | (2006.01) |
| *A61K 31/145* | (2006.01) |
| *A61K 31/185* | (2006.01) |
| *A61K 31/198* | (2006.01) |

(52) U.S. Cl.
CPC ............ *A61K 38/465* (2013.01); *A61K 9/0078* (2013.01); *A61K 31/10* (2013.01); *A61K 31/145* (2013.01); *A61K 31/185* (2013.01); *A61K 31/198* (2013.01); *C12Y 301/21001* (2013.01)

(58) Field of Classification Search
None
See application file for complete search history.

(56) References Cited

U.S. PATENT DOCUMENTS

| | | | |
|---|---|---|---|
| 6,348,343 B2 | 2/2002 | Lazarus et al. | |
| 8,236,786 B2 * | 8/2012 | Finch | A61K 9/0075 514/183 |
| 2010/0292505 A1 * | 11/2010 | Leveque | C07C 333/26 562/102 |

FOREIGN PATENT DOCUMENTS

| | | | | |
|---|---|---|---|---|
| EP | 1 004 302 A2 | 5/2000 | | |
| GB | WO 2011098799 A2 * | 8/2011 | ............ | A61K 9/0075 |
| GB | WO 2012025761 A1 * | 3/2012 | ............ | A61K 9/1623 |

OTHER PUBLICATIONS

Anonymous, "NCT01587001 on May 14, 2014 The effect of an oral antioxidant, N-Acetyl-L-Cysteine on Inflammatory and oxidative stress markers in pulmonary sarcoidosis," ClinicalTrials.gov Archive, May 14, 2014, pp. 1-3.

Boots, A. W. et al., "Antioxidant status associated with inflammatiopn in sarcoidosis: A potential role for antioxidants," Respiratory Medicine, Baillier Tindall, London GB, vol. 103, No. 3, Mar. 1, 2009. pp. 364-372.

Gressier, B. et al., "Comparison of in vitro effects of two thiol-containing drugs on human neutrophils hydrogen peroxide production, PubMed-NCBI," Methods Find Exp Clin Pharmacol., Jan. 1, 1993, pp. 101-105.

Paul, K. et al., "Effect of treatment with dornase alpha on airway inflammation in patients with cystic fibrosis," American Journal of Respiratory and Critical Care Medicine, vol. 169, No. 6, Mar. 15, 2004, pp. 719-725.

(Continued)

*Primary Examiner* — Robert Mondesi
*Assistant Examiner* — Richard Ekstrom
(74) *Attorney, Agent, or Firm* — Fox Rothschild LLP

(57) ABSTRACT

Methods of treating pulmonary sarcoidosis are described herein. Patients in need of treatment for pulmonary sarcoidosis are administered a therapeutically effective amount of a mucolytic agent such as DNase I. In some embodiments, the DNase I is a recombinant human DNase I such as dornase alfa.

13 Claims, 3 Drawing Sheets

(56) References Cited

OTHER PUBLICATIONS

Radomska-Lesniewska, D. M., "N-acetylcysteine inhibits IL-8 and MNP-9 release and ICAM-1 expression by bronchoalveolar cells from intestinal lung disease patients," Pharmacological Reports 2010, 62, 131-138.

Search Report from PCT/US2015/048606, mailed Apr. 12, 2016.
Tahanovich, Natallia et al., "P3435—The evaluation of oxygen-activating function of mononuclear phagocytes in sarcoidosis," 354 Clinical aspects in the management of sarcoidosis, Thematic poster session, Oct. 7, 2008, p. 596 (XP-002755409).
Written Opinion from PCT/US2015/048606, mailed Apr. 12, 2016.

* cited by examiner

```
          10         20         30         40         50
LKIAAFNIQTFGETKMSNATLVSYIVQILSRYDIALVQEVRDSHLTAVGK 60         70         80         90        100
LLDNLNQDAPDTYHYVVSEPLGRNSYKERYLFVYRPDQVSAVDSYYYDDG 110        120        130        140        150
CEPCGNDTFNREPAIVRFFSRFTEVREFAIVPLHAAPGDAVAEIDALYDV 160        170        180        190        200
YLDVQEKWGLEDVMLMGDFNAGCSYVRPSQWSSIRLWTSPTFQWLIPDSA 210        220        230        240        250
DTTATPTHCAYDRIVVAGMLLRGAVVPDSALPFNFQAAYGLSDQLAQAIS

260
DHYPVEVMLK
```

METHODS OF TREATING PULMONARY SARCOIDOSIS

CROSS-REFERENCE TO RELATED APPLICATIONS

This application claims priority from U.S. Provisional Patent Application Ser. No. 62/047,361, filed Sep. 8, 2014, the disclosures of which are incorporated herein by reference in their entirety.

FIELD OF THE INVENTION

The present invention is directed to methods for treating pulmonary sarcoidosis comprising the administration of mucolytic agents. In certain embodiments, the methods comprise administering a therapeutically effective amount of DNase I to a patient having pulmonary sarcoidosis.

BACKGROUND OF THE INVENTION

DNase I is an endonuclease found in mammals and other eukaryotes that cleaves phosphodiester linkages in DNA. It acts on single-stranded DNA, double-stranded DNA, and chromatin to reduce the size of DNA strands and yield 5'-phosphate-terminated polynucleotides with a free hydroxyl group. Human DNase I and certain variants are disclosed in U.S. Pat. Nos. 5,279,823; 6,348,343; and 6,391,607.

DNase I has been used to treat cystic fibrosis. Cystic fibrosis is a disease caused by mutations in a specific cellular chloride channel regulator, the cystic fibrosis transmembrane conductance regulator protein (CFTR). It is the most common autosomal recessive disease in Caucasians. The mutations prevent normal passage of $Cl^-$ ions through the chloride channel lumen of the airway epithelial cell membranes, resulting in a relative impermeability to chloride ions in the epithelial cells of the lungs and a depleted airway surface liquid volume. As a result of impaired function of the CFTR protein, mucus viscosity is increased and the thickened, tenacious secretions block the airways in the lungs of cystic fibrosis patients. The large amounts of viscous mucus blocking the airways in the lungs of cystic fibrosis patients causes a propensity for chronic infection, resulting in inflammation, progressive airway and parenchymal damage, bronchiectasis, pulmonary exacerbations, lung function decline and frequently premature death. Even though improved treatment has increased survival, the median predicted lifespan is only 35 years and patients experience significant morbidity and hospitalizations. Approximately 95% of cystic fibrosis deaths are due to lung infection.

In 1993, the U.S. Food and Drug Administration (FDA) approved a formulation of recombinant human DNase I for the treatment of cystic fibrosis. It was the first treatment approved by the FDA for cystic fibrosis in 30 years. The approved product is marketed in the U.S. by Genentech, Inc. under the brand name PULMOZYME®. PULMOZYME® is believed to act by cleaving DNA in the thick mucus secretions that are a hallmark of cystic fibrosis. This tends to liquefy the mucus, making it easier for the body to clear the mucus from the airways, with consequent improvement in airway function and lessened susceptibility to bacterial infections.

The success of PULMOZYME® in treating cystic fibrosis prompted its study in bronchiectasis, another lung disease where mucus buildup was thought to play a role. Unfortunately, a large clinical trial of bronchiectasis patients not only failed to demonstrate any benefit from PULMOZYME®, but suggested that such treatment was potentially harmful (O'Donnell, et al., 1998, Chest 113:1329-1334).

Sarcoidosis is a disease involving granulomas (abnormal collections of inflammatory cells), often present as nodules, which can form in various organs, including the skin, heart, liver, lungs, nervous system, and gastrointestinal tract. The granulomas are characterized by the accumulation of neutrophils, monocytes, macrophages, and activated T cells, as well as the production of elevated levels of inflammatory mediators such as tumor necrosis factor-α (TNF-α) interferon-γ, and interleukin-2.

The cause of sarcoidosis is unknown, but there is speculation that it is triggered by an immune reaction to some infectious or environmental antigen that continues after exposure to the antigen ceases. The lung is the most commonly involved organ in over 90% of cases. Most patients do not exhibit symptoms and are unaware that they have sarcoidosis. Half of all asymptomatic sarcoidosis patients are diagnosed after routine chest x-ray. The most common presenting symptoms are cough and dyspnea. The most common diagnostic clinical signs are: i) dyspnea, ii) cough, iii) skin rash, iv) inflammation of the eyes, v) weight loss, vi) fatigue, vii) fever, and viii) night sweats. Due to the non-specific nature of granulomas, sarcoidosis is generally diagnosed by excluding other diseases such as malignancies and infections. The lung in sarcoidosis typically displays the characteristic bilateral hilar lymphadenopathy on chest x-ray. Reversible stages of sarcoidosis (Scadding Radiographic Stages I and II), characterized by nodular reticular infiltrates and "ground-glass" appearance of lung parenchyma on chest x-ray, may not require treatment. Irreversible sarcoidosis (Stages III and IV), characterized by pulmonary cysts, diffuse parenchymal lung disease, honey comb lung structure (due to consolidation of alveoli) and bronchiectasis, has poor long-term prognosis and a high incidence of pulmonary exacerbations/relapses. Computerized tomography ("CT") findings for Stages III and IV include bronchiolar nodules (bronchovascular and subpleural), thickened interlobular septae, pulmonary architectural distortion and conglomerate masses. In the approximately 70% of sarcoidosis patients that do not require medical intervention, symptomatic treatment usually consists of non-steroidal anti-inflammatory drugs (NSAIDs) such as ibuprofen or aspirin; however, approximately one third of all patients develop a progressive form of chronic sarcoidosis that requires treatment. The first-line therapy for all such chronic sarcoidosis patients is oral steroids (e.g., prednisone or prednisolone) which have significant adverse side effects (susceptibility to infection, osteoporosis and rib fractures from coughing, diabetes, mental confusion, fluid retention, fatigue, etc.) and are not usable for chronic or long term therapy because of these adverse drug responses. In some patients, corticosteroids slow or reverse the course of the disease, but many patients may become refractory to steroids or do not respond at all. Those patients may experience frequent and severe respiratory infections associated with episodes of excessive coughing to dislodge and expel inspissated secretions and cell debris, including granulomas shed into the bronchial lumen. In corticosteroid non-responders with severe symptoms and no treatment options, other cytotoxic agents such as azathioprine, methotrexate, mycophenolic acid, and leflunomide may be tried. Of these, methotrexate is most widely used and is considered a first-line treatment in neurosarcoidosis, often in conjunction with corticosteroids. In general, the cytotoxic agents do not have benefits that outweigh their increased morbidity from cytotoxicity. The only definitive treatment for end-stage disease is lung transplantation and such patients with pulmonary sarcoidosis represent approximately 30% of all lung transplants conducted in the New York Presbyterian, Thoracic Surgery Lung Transplant Service (J.R. Sonnet, personal communication).

Some success in treating sarcoidosis with immunosuppressants has been observed. The rationale for such treatment is that the granulomas involved in sarcoidosis are caused by collections of immune system cells, particularly airway neutrophils and circulating T-cells. Infliximab, a monoclonal antibody that antagonizes the action of TNF-α, has been used to treat pulmonary sarcoidosis in clinical trials, with some success. Etanercept (another TNF-α antagonist), on the other hand, failed to demonstrate any significant efficacy in people with uveal sarcoidosis. The anti-TNF-α monoclonal antibody golimumab also failed to show any benefit in persons with pulmonary sarcoidosis. Adalimumab (yet another anti-TNF-α monoclonal antibody) induced a beneficial response in about half of sarcoidosis patients. See Baughman, et al., 2013, European Respiratory Journal 41:1424-1438.

Individualized therapy is a new paradigm in modern medicine as it transitions from "blockbuster" drugs to stratified personalized medicine. Unfortunately, this approach is not optimally supported by average results from large randomized clinical trials (RCTs). The n=1 approach confers extremely powerful assessment tools to achieve personalized medicine and, using this approach, the patient is the sole unit of observation in therapeutic assessment. The advantages accrued are several. First, in a single patient study, heterogeneity in design is tolerated as long as the single patient stratification arm results in objective evidence favoring the intervention, whereas large population-based RCTs require design uniformity to prevent confounding generalizations. Second, patients in an n=1 trial draw immediate benefit from the trial based on the optimal presentation and refinement of intervention strategies designed to benefit them objectively. This is totally dissimilar to a population-based RCT wherein an individual patient in physical distress may have received a placebo for the entire study period.

Surprisingly, the more powerful n=1 approach has only been used sparingly in general clinical and medical settings, even though it is born out of a recognition that medical interventions that work for a majority of chronic disease conditions have too often proven fruitless in RCTs (Jorgensen, 2008, Expert Rev. Mol. Diagn. 8(6):689-695; Jorgensen, 2009, Oncologist 14(5):557-558). There is a growing presumption that the clinical practice of medicine should recognize and embrace the unique individual characteristics of patients with rare diseases, often needing very costly treatment options, and strive to individualize patient care (Hu et al., 2005, Biotechniques 39(10 Suppl):S1-S6; Langreth & Waldholz, 1999, Oncologist 4(5):426-427; Trusheim et al., 2007, Nat. Rev. Drug Discov. 6(4):287-293).

In the present era of new drug development, large sample parallel group RCT's are often begun without detailed knowledge of the optimal therapeutic dose, patient selection criteria, and initial estimates of the proportion of patients that are responders (important for sample size determination), optimal outcomes on which subsequent trials should be based, safety for long-term/lifetime treatment, etc. In addressing many of these issues in the current environment, where detailed, individualized information is available for single patients, the US National Institutes of Health (NIH) has both advocated and acknowledged the utility of n=1 studies of patient responses to highly individualized therapy in forward-looking "precision medicine" evidence-based approaches. Individualized therapy improves outcome assessment because the treatment regimen is tailored to the patient's disease stratification. For example, the anticancer drug cetuximab (colorectal cancer) is ineffective if the KRAS protein in the tumor has a specific mutation (Van Cutsem et al., 2009, N. Engl. J. Med. 360(14):1408-1417) and the US FDA has relabeled the drug to require genetic profiling before use. Many other drugs have variations in effectiveness in certain patient strata that led to FDA relabeling (e.g., warfarin, carbamazepine, clopidogrel) (Flockhart et al., 2009, Clin. Pharmacol. Ther. 86(1):109-113; Topol, 2010, Sci. Transl. Med. 2(44):44 cm22). Furthermore, the FDA is actively developing streamlined review approaches to companion diagnostic tests with treatments where n=1 protocols facilitate the approval process (Hamburg & Collins, 2010, N. Engl. J. Med. 363(4): 301-304).

The n=1 clinical trial approach is very cost effective, but requires much more time commitment and supervision by medical professionals, coupled with suitably long observation intervals, coincident in the index patient with the normal time course of disease progression (interspersed with periodic "cessation of treatment" intervals (or "washout periods"), to test for spontaneous remission of disease). Not only is this targeted n=1 long-term study approach cost effective, but it has also resolved many confounding ambiguities of treatment that would be present in a population study, e.g., diet and lifestyle changes, progression/regression of disease, meaningful patient benefit, etc. The n=1 approach reflects the trend toward "personalized medicine" of the future and has a high degree of quasi-statistical precision because the patient serves as his or her own control, increasing confidence in the results of customized treatment. In fact, n=1 clinical studies could be deemed virtually essential for evaluation of highly targeted therapies, many of which may not even be amenable to RCTs because the between variance for treatments would be large relative to the relatively small sample size for an extremely rare disease. In such cases, the n=1 approach epitomizes the appropriateness of clinical trial designs which minimize the time a patient is given a suboptimal intervention. Moreover, sequential designs with lengthy data collection processes are especially useful for rare, unique diseases (Everitt & Pickler, 2004, Statistical Aspects of The Design of Clinical Trials. Imperial College Press; London, UK; Gerss & Kopcke, 2010, Adv. Exp. Med. Biol. 686:173-190; Meinert & Tonascia, 1986, Clinical Trials Design, Conduct, and Analysis Monographs in Epidemiology and Biostatistics. Vol. 469. Oxford University Press; NY, USA).

The ultimate clinically important issue for novel interventions with utility is generalizability of results to subpopulations. It is here that n=1 clinical trials excel, enabling stratification of patients into groups more or less likely to benefit from a specific treatment for population-level association studies (Barlow et al., Strategies for Studying Behavior for Change. 3. Vol. 393. Pearson/Allyn and Bacon; MA, USA; Guyatt et al., 1986, N. Engl. J. Med. 314(14):889-892). Individual variations in response to treatment reflect population variations and if stratifications are well described (Kraemer et al., 2002, Arch. Gen. Psychiatry 59(10):877-883; Kent & Hayward, 2007, JAMA 298(10):1209-1212; Scuffham et al., 2010, J. Gen. Intern. Med. 25(9):906-913), n=1 clinical trials objectively quantify this variability and provide informed guidance for treating individual patients using their own data. The efficiency of n=1 clinical trials in identifying and minimizing suboptimal treatments is far greater than standard care utilizing RCTs, both improving patient management and resulting in cost savings.

SUMMARY OF THE INVENTION

Described herein are methods of treating pulmonary sarcoidosis comprising administering to a patient in need thereof a therapeutically effective amount of a mucolytic agent. In certain embodiments, the mucolytic agent is DNase I, e.g., recombinant human DNase I (rhDNase I). In certain embodiments, the rhDNase I is the rhDNase I that is the active ingredient of PULMOZYME®.

In certain embodiments, the mucolytic agent is selected from the group consisting of: sodium 2-sulfanylethanesulfonate (mesna, marketed in the U.S. as UROMITEXAN®), disodium 2,2'disulfanediyldiethanesulfonate (dimesna), and combinations thereof.

In certain embodiments, the methods comprise administering DNase I and an additional mucolytic agent. In certain embodiments, the additional mucolytic agent is selected from the group consisting of mesna, dimesna, N-acetylcysteine, and combinations thereof. In addition to being mucolytic agents, mesna, dimesna, and N-acetylcysteine are free-radical scavengers. Pulmonary cellular antioxidant defense is significantly reduced with increased tissue levels of destructive free radicals in the inflammatory response to pulmonary sarcoidosis (Boots, et al., 2009, Resp. Med., 103:364). This finding points to the added utility of concomitant use of free-radical scavenging compounds such as mesna, dimesna and N-acetylcysteine. In those embodiments where a rhDNase I such as PULMOZYME is administered to the patient with an additional mucolytic agent, the rhDNase I may be administered before, after, or concomitantly with the additional mucolytic agent. Preferably, the rhDNase I is administered before or after the additional mucolytic agent. In some embodiments, rhDNase I is administered by nebulization and and mesna or dimesna is administered intravenously. In such embodiments, mesna or dimesna act as free-radical scavengers.

In certain embodiments, the methods treat a patient who has acute pulmonary sarcoidosis (patient diagnosed with sarcoidosis for <2 years). In certain embodiments, the methods treat a patient who has chronic pulmonary sarcoidosis (patient diagnosed with sarcoidosis for ≥2 years). In certain embodiments, the methods safely treat a patient with chronic pulmonary sarcoidosis for periods in excess of 12 years.

Patients that progress to chronic pulmonary sarcoidosis deteriorate fairly quickly due to recurrent infections/pulmonary fibrosis and don't generally live for 12 years. Treatment with a rhDNase I such as PULMOZYME® could be long-term (over 12 years) without progression of, or with minimal progression of, the disease or recurring pulmonary exacerbations. It is possible that the progression to pulmonary fibrosis and death may be precluded by preventing the recurrent airway infections with PULMOZYME®, effectively preventing the post-obstructive pneumonias and tissue damage by chemotactically attracted neutrophils that release neutrophilic proteases, inflammatory cytokines, nitric oxide, and oxygen free radicals (which collectively are probably responsible for the observed pulmonary fibrosis and emphysema-like loss of pulmonary real estate).

A key question relating to use of a rhDNAse I such as PULMOZYME® in pulmonary sarcoidosis patients is: "Is long-term use tolerated by the patient and does the clinical condition deteriorate as with untreated or steroid refractory disease?" The experimental results described herein—a patient who has undergone over 12 years of therapy with PULMOZYME® without side effects or incident, completely absent of any pulmonary exacerbations—indicate that the answer to this question is "Yes."

PULMOZYME® breaks the cycle of bronchial damage, impaired mucus clearance, recurrent inflammation and more damage—leading to pulmonary fibrosis and/or hemoptysis and death in the most seriously afflicted pulmonary sarcoid patients.

The methods described herein may improve the health of pulmonary sarcoidosis patients by decreasing the need for other medications (e.g., corticosteroids), reducing coughing, decreasing the number and severity of bacterial infections, improving the oxygen saturation of the patient's blood, and/or allowing for greater physical activity (e.g., improving exercise tolerance).

Certain embodiments of the invention include:

1. A method of treating pulmonary sarcoidosis comprising administering to a patient in need thereof a therapeutically effective amount of a mucolytic agent. Other embodiments include:

2. The method of embodiment 1 where the mucolytic agent is DNase I.

3. The method of embodiment 1 where the mucolytic agent is selected from the group consisting of: sodium 2-sulfanylethanesulfonate, disodium 2,2'-disulfanediyldiethanesulfonate, and combinations thereof.

4. The method of embodiment 1 where the DNase I is recombinant DNase I.

5. The method of embodiment 4 where the recombinant DNase I is recombinant human DNase I.

6. The method of embodiment 5 where the recombinant human DNase I is administering to the patient's lungs by inhalation.

7. The method of embodiment 6 where the inhalation carried out with the use of a nebulizer.

8. The method of embodiment 5 where the recombinant human DNase I has the amino acid sequence of native human DNase I.

9. The method of embodiment 5 where the recombinant human DNase I has the amino acid sequence of SEQ ID NO. 3.

10. The method of embodiment 1 where the pulmonary sarcoidosis is acute pulmonary sarcoidosis.

11. The method of embodiment 1 where the pulmonary sarcoidosis is chronic pulmonary sarcoidosis.

12. The method of embodiment 1 comprising administering an antibiotic to the patient.

13. The method of embodiment 1 comprising administering a bronchodilator to the patient.

14. The method of embodiment 1 comprising administering chest physical therapy or postural drainage to the patient.

15. The method of embodiment 4 comprising administering an additional mucolytic agent selected from the group consisting of: sodium 2-sulfanylethanesulfonate; disodium 2,2'-disulfanediyldiethanesulfonate; N-acetylcysteine to the patient; and combinations thereof.

BRIEF DESCRIPTION OF THE DRAWINGS

FIG. 1 shows the nucleotide (SEQ ID NO. 1) and deduced amino acid (SEQ ID NO. 2) sequences of human DNase I as reported in Shak et al., 1990, Proc. Natl. Acad. Sci. USA 87:9188-9192. Nucleotides are numbered at left. Amino acids are numbered above the line starting at Leu+1 of the mature enzyme sequence and preceded by a 22-amino-acid putative signal sequence (underlined). The four cysteine residues are printed in boldface. Two potential N-linked glycosylation sites are indicated by lines above the amino acid sequence.

FIG. 2 shows the amino acid sequence of native human DNase I (SEQ ID NO. 3) as reported in U.S. Pat. No. 6,348,343.

DETAILED DESCRIPTION

Figure 3:
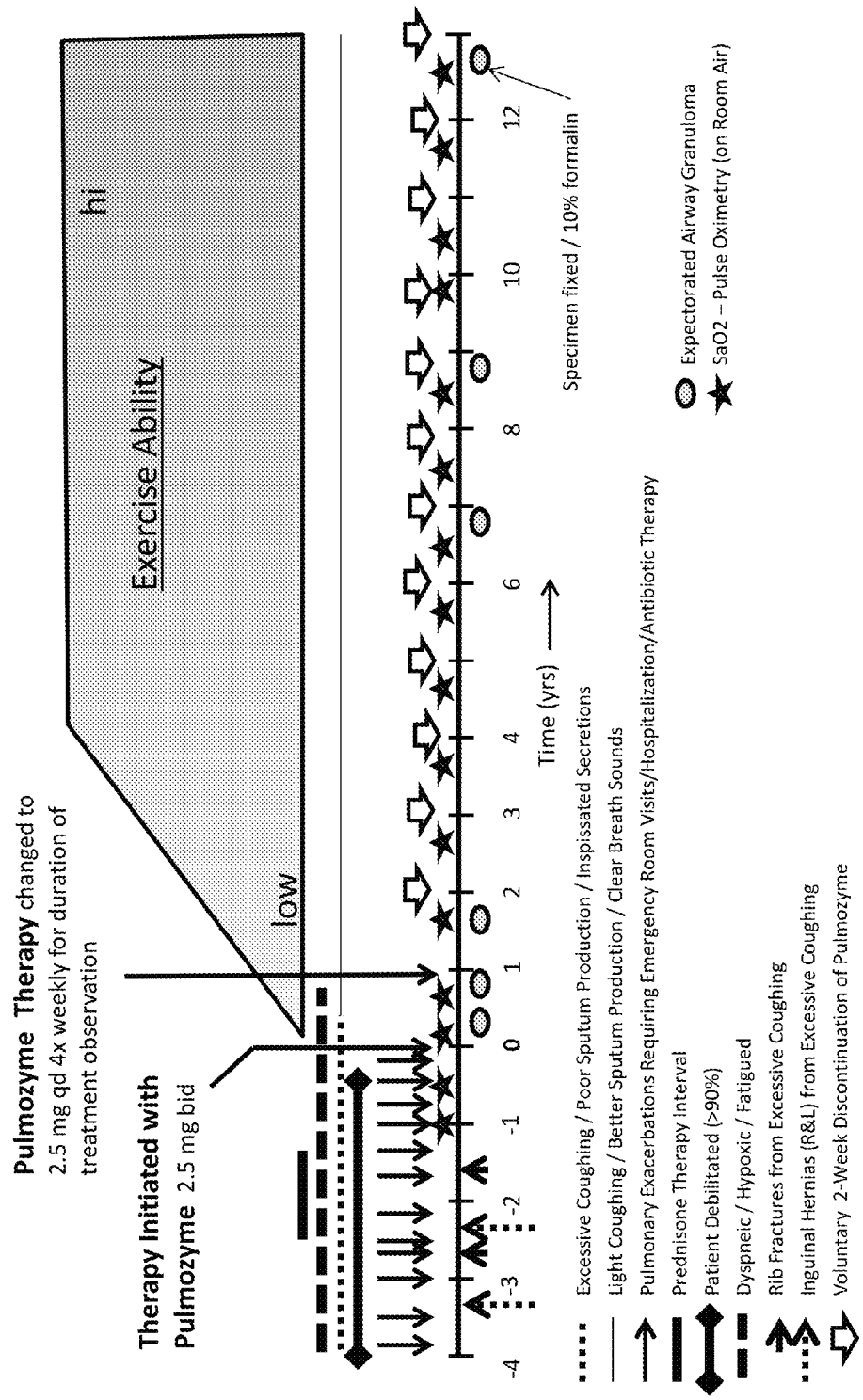
FIG. 3 shows the clinical timeline for the treatment of the patient in Example 1.

"DNA hydrolytic activity," as used herein, refers to the enzymatic activity of native human DNase I or a variant of human DNase I to cleave DNA to yield 5'-phosphorylated oligonucleotide end products.

"Mucolytic agent," as used herein, refers to an agent used to dissolve mucus in order to help loosen and clear the mucus from the airways of the lung.

"Patient," as used herein, refers to a human patient.

"rhDNase I," as used herein, refers to recombinant human DNase I, i.e., human DNase I that is obtained by expressing a DNA construct encoding human DNase I in certain host cells such as Chinese hamster ovary (CHO) cells.

"A variant of human DNase I," as used herein, refers to a polypeptide that comprises an amino acid sequence that is different from that of native human DNase I but still retains at least 90% amino acid sequence identity with native human DNase I.

"Therapeutically effective amount," as used herein, refers to an amount of mucolytic agent that provides a therapeutic benefit in the treatment or management of pulmonary sarcoidosis, e.g., by delaying or minimizing one or more symptoms associated with pulmonary sarcoidosis, or by enhancing the therapeutic benefit provided by another therapeutic agent for pulmonary sarcoidosis.

In one embodiment, the form of rhDNase I used in the methods described herein is that found in PULMOZYME®, which contains a highly purified aqueous solution of rhDNase I obtained from Chinese hamster ovary (CHO) cells genetically engineered to express native human DNase I. The rhDNase I in PULMOZYME® is a glycoprotein containing 260 amino acids with a molecular weight of 37,000 daltons. The primary amino acid sequence of this protein is identical to that of native human DNase I. Its generic name is dornase alfa. In certain embodiments, PULMOZYME® is administered to pulmonary sarcoidosis patients in the same general manner (e.g., dosage, method of administration) that it is administered to cystic fibrosis patients. In one embodiment, the form of rhDNase I used in the methods described herein is a biosimilar of PULMOZYME®.

The DNA and amino acid sequences of native human DNase I can be found in Shak et al., 1990, Proc. Natl. Acad. Sci. USA 87:9188-9192 (Shak). Also found in Shak is a detailed description of how a nucleotide encoding human DNase I may be obtained by cloning in λgt10 from a human pancreatic cDNA library and how that nucleotide may be recombinantly expressed. These disclosures of Shak are incorporated by reference herein. FIG. 1A of Shak shows the DNA and amino acid sequences of native human DNase I and is reproduced herein as FIG. 1 of this application.

As an alternative to the rhDNase I found in PULMOZYME®, the methods described herein may be practiced by administering a different rhDNase I. For example, U.S. Pat. No. 5,279,823 describes a deamidated rhDNase I that may be used. U.S. Pat. No. 6,348,343 describes rhDNase I variants having slightly different amino acid sequences from that found in native human DNase I that may be used in the methods for treating pulmonary sarcoidosis described herein. For example, described are the following:

variants of human DNase I (SEQ ID NO: 3) comprising at least one amino acid substitution at the following positions corresponding to the sequence of native human DNase I: His44, Leu45, Val48, Gly49, Leu52, Asp53, Asn56, His64, Tyr65, Val66, Val67, Ser68, Glu69, Ser94, Tyr96 or Ala 114, wherein said variants have DNA hydrolytic activity;

variants of human DNase I having amino acid sequences that are at least 99% identical to SEQ ID NO: 3, wherein said variants have DNA hydrolytic activity;

variants of human DNase I having amino acid sequences that are at least 95% identical to SEQ ID NO: 3, wherein said variants have DNA hydrolytic activity;

variants of human DNase I having amino acid sequences that are at least 90% identical to SEQ ID NO: 3, wherein said variants have DNA hydrolytic activity;

variants of human DNase I having amino acid sequences that differ from SEQ ID NO: 3 by only one amino acid substitution, wherein said variants have DNA hydrolytic activity;

variants of a human DNase I (SEQ ID NO: 3) comprising at least one amino acid substitution selected from the group consisting of: E13A, E13H, E13R, E13W, E13Y, H44A, H44D, H44Y, H44W, H44C, H44Q, H44N, H44E, L45C, L45K, L45R, V48C, V48K, V48R, G49C, G49I, G49K, G49R, G49Y, L52C, L52K, L52M, L52N, L52R, D53A, D53K, D53R, D53Y, D53C, D53L, D53M, N56C, N56F, N56K, N56R, N56W, D58T, H64N, Y65A, Y65R, Y65W, Y65C, Y65K, Y65M, Y65S, Y65N, Y65E, Y65P, V66T, V66N, V67A, V67E, V67K, V67C, V67D, V67H, V67M, V67P, V67R, V67S, V67T, V67N, S68K, S68R, S68M, S68N, E69K, E69R, E69A, E69C, E69M, E69T, P70T, S94N, Y96T, A114C, A114E, A114G, A114H, A114K, A114L, A114M, A114Q, A114R, A114W and A114Y, where said variant has DNA hydrolytic activity;

variants of a human DNase I (SEQ ID NO: 3) comprising at least one amino acid substitution selected from the group consisting of: E13A, E13H, E13R, E13W, E13Y, H44A, G49R, D53R, D53K, D53Y, D53A, D53C, N56R, Y65A, Y65R, Y65W, V67E, E69K, E69R A114G and A114H; and variants of a human DNase I (SEQ ID NO: 3) comprising at least one amino acid substitution selected from the group consisting of: H44A:D53R:Y65A, H44A:Y65A:E69R, D53R:Y65A, D53R:E69R, S94N:Y96T, V67N:E69T, Y65N: V67T and H64N:V66T.

U.S. Pat. No. 6,391,607 also describes rhDNase I variants having slightly different amino acid sequences from that found in native human DNase I that may be used in the methods for treating pulmonary sarcoidosis described herein. For example, described are human DNase I variants comprising amino acid sequences having at least 90% identity with the amino acid sequence of native human DNase I (SEQ ID NO: 3) and a substitution at one or more amino acid residues corresponding to Gln9, Thr14, Asn74, Ser75, and Thr205 of native human DNase I.

rhDNase I may be produced recombinantly in Chinese hamster ovary (CHO) cells by growing CHO cells that have been transfected with a suitable expression vector encoding human DNase I in a suitable medium and purifying the rhDNase I by conventional means, e.g., by tangential flow filtration and column chromatography. Alternatively, rhDNase I may be produced using other suitable recombinant host cells, as is well known in the art.

The mucolytic agents used in the methods described herein may be administered to the lungs by inhalation using a suitable nebulizer or nebulizer/compressor system. Suitable nebulizer/compressor systems include the following:

Hudson T UP-DRAFT II® nebulizer with PULMO-AIDE® compressor;

Marquest ACORN II® nebulizer with PULMO-AIDE® compressor;

PARI LC® Jet+ nebulizer with PARI PRONEB® compressor;

PARI BABY® nebulizer with PARI PRONEB® compressor;

Durable SIDESTREAM® nebulizer with MOBILAIRE® compressor; and

Durable SIDESTREAM® nebulizer with PORTA-NEB® compressor.

When the mucolytic agent is DNase I, a dose of about 2.5 mg once daily may be used. Alternatively, a dose of about 2.5 mg twice daily may be used. Other doses that may be used include about 0.5 mg, about 1.0 mg, about 1.5 mg, about 2.0 mg, about 2.5 mg, about 3.0 mg, about 3.5 mg, about 4.0 mg, about 4.5 mg, or about 5.0 mg, either once or twice per day. Doses of 0.5 mg to 5.0 mg, 1.0 mg to 4.0 mg, or 1.5 mg to 3.5 mg, either once or twice per day, may also be used.

In certain embodiments, the mucolytic agent is delivered by inhalation to the patient 1, 2, 3, 4, 5, 6, or 7 times per week for a certain time period. In certain embodiments, the time period is about 1 week, about 2 weeks, about 1 month, about 2 months, about 3 months, about 6 months, about 9 months, about 1 year, about 2 years, about 3 years, about 4 years, about 5 years, about 6 years, about 7 years, about 8 years, about 9 years, about 10 years, about 11 years, or about 12 years.

Pharmaceutical compositions comprising a therapeutically effective amount of rhDNase I and a pharmaceutically acceptable carrier or excipient may be administered to patients in need of treatment for pulmonary sarcoidosis according to the methods described herein. A buffered or unbuffered aqueous solution of DNase I, e.g., an isotonic salt solution such as 150 mM sodium chloride containing 1.0 mM calcium chloride at pH 7, may be a suitable pharmaceutical composition.

In one embodiment, rhDNase I is administered as a sterile, aqueous solution containing 1.0 mg/mL dornase alfa, 0.15 mg/mL calcium chloride dehydrate, and 8.77 mg/mL sodium chloride with no preservative. The nominal pH of the solution is 6.3. In one embodiment, the rhDNase I is supplied in single-use ampoules that deliver 2.5 mL of this solution through a nebulizer.

In certain embodiments, the methods comprise administering a mucolytic agent and an oral corticosteroid, e.g., prednisone or prednisolone, to a patient in need of treatment for pulmonary sarcoidosis. In certain embodiments, the methods comprise administering a mucolytic agent and a bronchodilator to a patient in need of treatment for pulmonary sarcoidosis.

In certain embodiments, the methods comprise administering a mucolytic agent and an antibiotic to a patient with pulmonary sarcoidosis. The mucolytic agent may be DNase I and the antibiotic may be selected from the group consisting of TOBREX®, TOBI®, tobramycin, AKTOB®, BETHKIS®, TOBI® Podhaler, PROVENTIL®, VENTOLIN®, albuterol, ZITHROMAX®, azithromycin, Azasite, Cotazym, CREON®, ZENPEP®, Pancreaze, PERTZYE®, ULTRESA®, VIOKASE®, Nebcin, and combinations thereof. The antibiotic may be administered by inhalation, e.g., using a nebulizer. The antibiotic may be administered together with, or separately from, the mucolytic agent.

In certain embodiments, the mucolytic agent is administered with non-pharmaceutical therapies typically used to treat pulmonary sarcoidosis (e.g., chest physical therapy and/or postural drainage).

EXAMPLE

A patient (middle aged female, African ancestry) had a history of debilitating chronic pulmonary sarcoidosis with multiple pulmonary exacerbations requiring antibiotic therapy yearly. Constant coughing resulted in fractured ribs and abdominal hernias. At times, the patient was bedridden, dyspneic, and could not climb stairs or walk more than 10 feet. Steroids had been prescribed by pulmonary specialists; however the side effects of steroid therapy (diabetes, weight gain, memory loss, mental confusion, crippling joint pain) were intolerable. The patient's pulmonary sarcoidosis was deemed ultimately refractory to steroid therapy, which was discontinued, leaving essentially no therapeutic options for this patient.

PULMOZYME® was prescribed to the patient by a licensed medical practitioner to initiate treatment. The patient responded to PULMOZYME® treatment as follows:

1. Adverse events relating to PULMOZYME®—none in more than 10 years of treatment;

2. Coughing, wheezing, dyspnea—none (although continued PULMOZYME® therapy has been required 3-4 days/week to maintain improved pulmonary function, which immediately begins to regress with periodic attempts to discontinue therapy);

3. At present, arterial $O_2$ saturation is 98% on room air (finger pulse oximetry);

4. Exercise tolerance during treatment—unlimited;

5. Pulmonary exacerbations (pneumonia)—none in more than 10 years of treatment;

6. Granuloma formation/expectoration—occasional;

7. Emergency room visits an hospitalizations relating to pulmonary sarcoidosis—none in more than 10 years of treatment;

8. Blood chemistry, liver and kidney function during treatment—normal;

9. Unrelated clinical conditions treated during PULMOZYME® therapy:
   a. Abdominal hysterectomy with spinal anesthesia;
   b. Sinusitis—two episodes treated with antihistamines;
   c. Chest wall lipoma—surgically removed under local anesthetic;
   d. Posterior knee lipoma—surgically removed under local anesthetic;

10. Chest physical therapy with postural drainage—none required during PULMOZYME® therapy;

11. Rib fractures and abdominal hernias—none during PULMOZYME® therapy;

12. General quality of life—vastly improved during PULMOZYME® therapy.

These clinical findings for treatment of chronic pulmonary sarcoidosis are even more noteworthy because black, female patients typically have more serious pulmonary involvement with a poor long-term prognosis and very high incidence of relapses.

The extended clinical timeline for the patient described above was appropriate, given the nature of pulmonary sarcoidosis. Approximately 50% of all pulmonary sarcoidosis patients experience remission within 2 years of the onset of symptoms. It is generally accepted that Scadding radiologic staging on presentation of the disease predicts the approximate likelihood of remission. In some instances, remission follows oral steroid therapy, but in all cases the causes for remission are unknown. Pulmonary fibrosis (Stage IV) patients do not experience remission and only a small percentage of patients with chronic pulmonary sarcoidosis (20%±) undergo remission.

While true remission of disease in pulmonary sarcoidosis is not predictable, end-stage disease typically progresses over a 5-10 year period as the patient's condition gradually deteriorates. The typical clinical course for chronic pulmonary sarcoidosis is a continual deterioration of pulmonary function, culminating in acute respiratory failure (ARF) due variously to either: i) lung parenchymal destruction; ii) hemoptysis; iii) pneumonia; or, iv) interstitial fibrosis.

The worst clinical prognosis was associated the patient described above:
  i) Age>40 at onset of disease
  ii) African-American ancestry
  iii) Female
  iv) Requirement for steroids
  v) Skin/neurologic involvement
  vi) Stage II-IV chest radiograph
  vii) Significant lung function impairment
  viii) Recurrent pneumonias requiring ER visits, antibiotics, hospitalization, etc.
  ix) Severe dyspnea with inspissated secretions on presentation The extended clinical timeline described above allowed for a distinction between remission and stabilization of the disease to be made. One way to distinguish patients that are in remission from those that have had their disease stabilized and are being maintained in a quasi-steady state by the therapeutic intervention is to observe treatment over a suitably long interval (perhaps equivalent to the interval leading to ARF and death) and periodically discontinue therapy to observe whether the disease symptoms worsen or remain unchanged, thereby indicating true remission of disease. This was done on an annual basis for the patient described above for the typical "survival window" (8-14 years for patients with progressive, chronic disease).

The clinical timeline for treatment of the patient described above with PULMOZYME® is represented diagrammatically in FIG. 3 during pretreatment and for the entire treatment interval. During treatment there has not been a single pulmonary exacerbation, although the patient has had several surgeries and several short-duration upper respiratory tract infections with nasal congestion, headache, and malaise. Arterial oxygenation via pulse oximetry improved from a low of $SaO_2$=70% during the pre-PULMOZYME® treatment interval to the currently measured $SaO_2$=99% on room air, coincident with the gradual improvement in exercise ability and disappearance of dyspnea on exertion. The patient voluntarily discontinued therapy with PULMOZYME® for 2-week intervals every year during the treatment period to determine whether regression of disease has occurred or if continued therapy with PULMOZYME® is necessary. In each instance of discontinuation of PULMOZYME® therapy, the patient's pulmonary disease symptoms (dyspnea, inspissated secretions, etc.) worsened, but were resolved upon resumption of PULMOZYME® therapy (2.5 mg qd 4× weekly). Occasionally the patient reported expectoration of "lumps" of lung tissue, presumably shed airway granulomas, and the most recent specimen was recovered and fixed in 10% formalin for histopathology. The patient's routine chest x-rays have shown improvement during treatment, with evidence of scarring that has not progressed to more severe disease. The only temporary coughing episodes noted during PULMOZYME® therapy have been associated with periodic bronchial irritation due to mucus plugs and/or expectoration of shed granulomas, none of which were severe enough to result in abdominal hernia pain or rib fractures. The patient's sarcoid skin involvement is unchanged and the patient's diet has been unrestricted. The patient is currently in a good state of health, enjoying a markedly improved quality of life, but must continue therapy with PULMOZYME® for the foreseeable future on the maintenance schedule of 2.5 mg qd, 4×-5× weekly.

Observations of this single patient over a long time period, with close monitoring of the clinical signs and symptoms of this disease, demonstrated dramatic treatment-related improvements in quality of life, the complete absence of pulmonary exacerbations, and remarkable improvement in blood oxygenation/exercise tolerance. Remission of disease was not evident in this patient, since annual discontinuation of therapy with PULMOZYME® for 14 days resulted in worsening of disease symptoms in every instance (increased coughing, dyspnea, and physical discomfort). This sequential, long-term monitoring provides a very high degree of confidence in the beneficial results of PULMOZYME® therapy and a complete absence of side effects associated with long-term use.

Due to the progressive nature of chronic pulmonary sarcoidosis and the very low probability of remission for this patient, it would have been difficult to draw meaningful conclusions from observations over a short period of PULMOZYME® therapy. Instead, an extended period of serial observations was carried out, since only a single patient was studied and there was no test or indicator that could be used to evaluate the progression or remission status of the disease in a single patient—other than discontinuation of therapy.

Six fundamentally important questions were affirmatively addressed in the treatment described above:

1. Does the short treatment interval (1 yr) predict the long term response (10 yrs) when lifetime therapy is anticipated (Kravitz et al., 2009, Contemp. Clin. Trials 30(5):436-445)?

2. Can the therapeutic intervention be tolerated indefinitely without an adverse drug response (ADR)?

3. Will the experimental design be able to separate spontaneous remission of disease from the continuing need for maintenance therapy in a steady-state patient disequilibrium?

4. Is the improvement in patient quality of life justified by the cost and effort required by therapy and what are the assessment tools needed to evaluate long-term treatment?

5. Can the n=1 trial be continued until treatment efficacy and tolerability is either established or disproved (Guyatt et al., 1986, N. Engl. J. Med. 314(14):889-892; Rochon, 1990, J. Clin. Epidemiol. 43(5):499-508)?

6. Can the n=1 results be used to develop stratified treatment arms for subsequent larger population based RCT's that would be essential for formal marketing approval of the therapeutic intervention by the US FDA?

In answering the above questions, the objective was to utilize this n=1 stratified medicine approach for the index chronic pulmonary sarcoidosis patient to support initiatives that facilitate "evidence-based" medicine (Guyatt et al., 2000, Evidence-Based Medicine Working Group, JAMA 284(10): 1290-1296; Sackett et al., 1996, BMJ 312(7023):71-72; Lauer & Collins, 2010, JAMA 303(21):2182-2183; Collins, 2010, Science 327(5961):36-37) and, more importantly, quickly maximize therapeutic precision for a patient in severe distress with no alternative treatment options. The overarching goal was to determine the optimal individualized treatment using objective, results-driven criteria evolved over the course of therapy. Based on the objective results of this n=1 trial, this patient has helped to provide key insights into identifying how individual outcomes might be improved within the larger heterogeneous at-risk population by establishing individual treatment stratifications based on specific clinical risk profiles and the stage and spectrum of disease. Furthermore, as a part of the individualized therapy, annual no-treatment ("washout") intervals with the index patient were utilized over time to periodically evaluate the continued benefits of long-term therapy.

One downside to the n=1 clinical trial is the constant, long-term monitoring required and associated patient recruitment and retention issues. For the index patient in this application, recruitment, retention and compliance were not a problem since no alternative therapy existed and the patient's distressed condition at the outset gave rise to a discouraging, steadily declining medical prognosis coupled with an unwillingness on the part of the patient to undergo long periods of suboptimal treatment with previously attempted ineffective standard care (see the Clinical Timeline shown in FIG. 3).

A second downside to the n=1 clinical trial relates to the confounding effects of lifestyle changes (dietary modification, other healthcare issues, exercise regimens, etc.) on interpretation of treatment results. But these confounding variables were essentially averaged out over time for the index patient. It is here that increasing the length of the trial (see Clinical Timeline) clearly resolved ambiguities relating to confounding variable effects, including the possibility of spontaneous remission of disease. Washout periods (annual 2-week "no-treatment" intervals) were invariably associated with return of disease symptoms, indicating that the index chronic pulmonary sarcoidosis patient may be analogous to the CF patient requiring quasi-daily therapy; furthermore, the patient's subjective experience confirmed the utility of treatments and adverse drug responses (ADRs) were not observed over the entire treatment interval reported herein.

PULMOZYME® is clearly validated as a safe and effective life-long treatment regimen based upon the study length and the index patient's subjective and objective responses. It should be noted that the patient was monitored daily during washout intervals to avoid compromising patient safety—an approach analogous to the placebo arm of a RCT. In addition, the patient was instructed to immediately resume treatment if her physical condition (dyspnea, excessive coughing, discolored mucus, etc.) deteriorated. Typically, these disease symptoms began to recur between week 1 and week 2, prior to the end of the 2 week washout interval.

From the long-term results of this index patient, it is evident that certain stratifications of future patient groups in a standard RCT would be appropriate, although such efforts would likely cost tens of millions of dollars, involve multiple international clinical centers, and a reasonably large clinical research team. The work presented herein is key to establishing the next phase of clinical studies, raising sufficient funding and completing RCTs that would hopefully lead to US FDA approval of PULMOZYME® for use in chronic pulmonary sarcoidosis. Recognizing that the USA is in the grip of a healthcare crisis has motivated serious calls for advances in medical research (Collins, 2010, Science 327(5961):36-37) and adoption of precision medicine approaches for rare diseases, of which chronic pulmonary sarcoidosis is one that has stubbornly defied successful treatment until now.

Long-term PULMOZYME® therapy of the above patient has been demonstrated to dramatically reduce the morbidity of chronic pulmonary sarcoidosis and to improve quality of life. Disease remission does not appear to have occurred during the treatment interval for this patient and clinical improvement was entirely dependent upon continued PULMOZYME® therapy. While symptoms of pulmonary sarcoidosis have been and remain mitigated for this patient, the underlying cause of the disease remains and there is potential for rapid disease progression upon discontinuation of therapy.

What is claimed is:

1. A method of treating pulmonary sarcoidosis comprising administering to a patient in need thereof a therapeutically effective amount of DNase I.

2. The method of claim 1 where the DNase I is recombinant DNase I.

3. The method of claim 2 where the recombinant DNase I is recombinant human DNase I.

4. The method of claim 3 where the recombinant human DNase I is administered to the patient's lungs by inhalation.

5. The method of claim 4 where the inhalation is carried out with the use of a nebulizer.

6. The method of claim 3 where the recombinant human DNase I has the amino acid sequence of native human DNase I.

7. The method of claim 3 where the recombinant human DNase I has the amino acid sequence of SEQ ID NO. 3.

8. The method of claim 1 where the pulmonary sarcoidosis is acute pulmonary sarcoidosis.

9. The method of claim 1 where the pulmonary sarcoidosis is chronic pulmonary sarcoidosis.

10. The method of claim 1 further comprising administering an antibiotic to the patient.

11. The method of claim 1 further comprising administering a bronchodilator to the patient.

12. The method of claim 1 further comprising administering chest physical therapy or postural drainage to the patient.

13. The method of claim 2 further comprising administering to the patient an agent selected from the group consisting of: sodium 2-sulfanylethanesulfonate; disodium 2,2'-disulfanediyldiethanesulfonate; N-acetylcysteine; and combinations thereof.

* * * * *

```
                              SEQUENCE LISTING

<160> NUMBER OF SEQ ID NOS: 3

<210> SEQ ID NO 1
<211> LENGTH: 1039
<212> TYPE: DNA
<213> ORGANISM: Homo sapiens
<220> FEATURE:
<221> NAME/KEY: CDS
<222> LOCATION: (160)..(1005)

<400> SEQUENCE: 1
tcctgcacag gcagtgcctt gaagtgcttc ttcagagacc tttcttcata gactactttt       60
ttttctttaa gcagcaaaag gagaaaattg tcatcaaagg atattccaga ttcttgacag      120
cattctcgtc atctctgagg acatcaccat catctcagg atg agg ggc atg aag         174
                                            Met Arg Gly Met Lys
                                              1               5 ctg ctg ggg gcg ctg ctg gca ctg gcg gcc cta ctg cag ggg gcc gtg       222
Leu Leu Gly Ala Leu Leu Ala Leu Ala Ala Leu Leu Gln Gly Ala Val
                 10                  15                  20 tcc ctg aag atc gca gcc ttc aac atc cag aca ttt ggg gag acc aag       270
Ser Leu Lys Ile Ala Ala Phe Asn Ile Gln Thr Phe Gly Glu Thr Lys
             25                  30                  35 atg tcc aat gcc acc ctc gtc agc tac att gtg cag atc ctg agc cgc       318
Met Ser Asn Ala Thr Leu Val Ser Tyr Ile Val Gln Ile Leu Ser Arg
         40                  45                  50 tat gac atc gcc ctg gtc cag gag gtc aga gac agc cac ctg act gcc       366
Tyr Asp Ile Ala Leu Val Gln Glu Val Arg Asp Ser His Leu Thr Ala
     55                  60                  65 gtg ggg aag ctg ctg gac aac ctc aat cag gat gca cca gac acc tat       414
Val Gly Lys Leu Leu Asp Asn Leu Asn Gln Asp Ala Pro Asp Thr Tyr
70                  75                  80                  85
```

-continued

| | | |
|---|---|---|
| cac tac gtg gtc agt gag cca ctg gga cgg aac agc tat aag gag cgc<br>His Tyr Val Val Ser Glu Pro Leu Gly Arg Asn Ser Tyr Lys Glu Arg<br>                           90                       95                  100 | 462 |
| tac ctg ttc gtg tac agg cct gac cag gtg tct gcg gtg gac agc tac<br>Tyr Leu Phe Val Tyr Arg Pro Asp Gln Val Ser Ala Val Asp Ser Tyr<br>                105                    110                115 | 510 |
| tac tac gat gat ggc tgc gag ccc tgc ggg aac gac acc ttc aac cga<br>Tyr Tyr Asp Asp Gly Cys Glu Pro Cys Gly Asn Asp Thr Phe Asn Arg<br>                120                    125                130 | 558 |
| gag cca gcc att gtc agg ttc ttc tcc cgg ttc aca gag gtc agg gag<br>Glu Pro Ala Ile Val Arg Phe Phe Ser Arg Phe Thr Glu Val Arg Glu<br>  135                      140                    145 | 606 |
| ttt gcc att gtt ccc ctg cat gcg gcc ccg ggg gac gca gta gcc gag<br>Phe Ala Ile Val Pro Leu His Ala Ala Pro Gly Asp Ala Val Ala Glu<br>150                      155                    160                165 | 654 |
| atc gac gct ctc tat gac gtc tac ctg gat gtc caa gag aaa tgg ggc<br>Ile Asp Ala Leu Tyr Asp Val Tyr Leu Asp Val Gln Glu Lys Trp Gly<br>                170                    175                180 | 702 |
| ttg gag gac gtc atg ttg atg ggc gac ttc aat gcg ggc tgc agc tat<br>Leu Glu Asp Val Met Leu Met Gly Asp Phe Asn Ala Gly Cys Ser Tyr<br>            185                    190                195 | 750 |
| gtg aga ccc tcc cag tgg tca tcc atc cgc ctg tgg aca agc ccc acc<br>Val Arg Pro Ser Gln Trp Ser Ser Ile Arg Leu Trp Thr Ser Pro Thr<br>        200                    205                  210 | 798 |
| ttc cag tgg ctg atc ccc gac agc gct gac acc aca gct aca ccc acg<br>Phe Gln Trp Leu Ile Pro Asp Ser Ala Asp Thr Thr Ala Thr Pro Thr<br>  215                      220                    225 | 846 |
| cac tgt gcc tat gac agg atc gtg gtt gca ggg atg ctg ctc cga ggc<br>His Cys Ala Tyr Asp Arg Ile Val Val Ala Gly Met Leu Leu Arg Gly<br>230                      235                    240                245 | 894 |
| gcc gtt gtt ccc gac tcg gct ctt ccc ttt aac ttc cag gct gcc tat<br>Ala Val Val Pro Asp Ser Ala Leu Pro Phe Asn Phe Gln Ala Ala Tyr<br>                250                    255                260 | 942 |
| ggc ctg agt gac caa ctg gcc caa gcc atc agt gac cac tat cca gtg<br>Gly Leu Ser Asp Gln Leu Ala Gln Ala Ile Ser Asp His Tyr Pro Val<br>        265                    270                  275 | 990 |
| gag gtg atg ctg aag tgagcagccc ctccccacac cagttgaact gcag<br>Glu Val Met Leu Lys<br>        280 | 1039 |

<210> SEQ ID NO 2
<211> LENGTH: 282
<212> TYPE: PRT
<213> ORGANISM: Homo sapiens

<400> SEQUENCE: 2

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

```
Ser Tyr Lys Glu Arg Tyr Leu Phe Val Tyr Arg Pro Asp Gln Val Ser
            100                 105                 110

Ala Val Asp Ser Tyr Tyr Asp Asp Gly Cys Glu Pro Cys Gly Asn
        115                 120                 125

Asp Thr Phe Asn Arg Glu Pro Ala Ile Val Arg Phe Phe Ser Arg Phe
130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Trp Thr Ser Pro Thr Phe Gln Trp Leu Ile Pro Asp Ser Ala Asp Thr
    210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
        260                 265                 270

Asp His Tyr Pro Val Glu Val Met Leu Lys
            275                 280

<210> SEQ ID NO 3
<211> LENGTH: 260
<212> TYPE: PRT
<213> ORGANISM: Homo sapiens

<400> SEQUENCE: 3

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
            100                 105                 110

Pro Ala Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190
```

-continued

```
Gln Trp Leu Ile Pro Asp Ser Ala Asp Thr Thr Ala Thr Pro Thr His
        195             200             205

Cys Ala Tyr Asp Arg Ile Val Val Ala Gly Met Leu Leu Arg Gly Ala
        210             215             220

Val Val Pro Asp Ser Ala Leu Pro Phe Asn Phe Gln Ala Ala Tyr Gly
225             230             235             240

Leu Ser Asp Gln Leu Ala Gln Ala Ile Ser Asp His Tyr Pro Val Glu
            245             250             255

Val Met Leu Lys
        260
```